(12) United States Patent
Duffy

(10) Patent No.: US 9,144,480 B2
(45) Date of Patent: Sep. 29, 2015

(54) LIGHT-EMITTING WAND WITH ELECTRICALLY-CONDUCTIVE HEAT SINKS

(75) Inventor: Robert F. Duffy, Stafford Springs, CT (US)

(73) Assignee: Schott Corporation, Elmsford, NY (US)

( * ) Notice: Subject to any disclaimer, the term of this patent is extended or adjusted under 35 U.S.C. 154(b) by 542 days.

(21) Appl. No.: 13/411,885

(22) Filed: Mar. 5, 2012

(65) Prior Publication Data

US 2012/0230017 A1 Sep. 13, 2012

Related U.S. Application Data

(60) Provisional application No. 61/464,930, filed on Mar. 11, 2011.

(51) Int. Cl.
*A61C 13/15* (2006.01)
*F21V 19/00* (2006.01)
(Continued)

(52) U.S. Cl.
CPC ..... *A61C 19/004* (2013.01); *A61B 2017/00734* (2013.01); *A61B 2019/521* (2013.01); *F21V 19/001* (2013.01); *F21V 29/2212* (2013.01); *G02B 19/0061* (2013.01)

(58) Field of Classification Search
CPC .......... F21Y 2101/02; F21Y 2103/003; F21Y 2113/007; F21Y 2111/004; F21V 29/004; F21V 29/70; F21V 29/75; F21V 29/773; F21V 29/74; F21V 29/006; F21V 29/89; F21V 23/005; F21V 29/2212; F21V 29/713; F21V 29/763; F21V 23/006; F21V 23/06; F21V 29/20; F21V 23/00; F21V 19/001; F21V 21/35; F21V 29/002; F21V 29/02; F21V 29/30; F21V 23/001; F21V 29/15; F21V 29/402; F21V 29/58; F21V 29/76; F21V 29/77; F21V 29/777; F21V 29/78; H01L 2224/73265; H01L 25/0753; H01L 33/62; H01L 33/64; H01L 33/38; H01L 2224/32245; H01L 2224/45124; H01L 2224/45144; H01L 2924/12041; H01L 33/48; H01L 23/49861; F21K 9/00; F21K 9/135; F21K 9/30; F21K 9/50; F21K 9/52; F21K 9/54; H05K 2201/10106; H05K 1/0203; H05K 1/181; H05K 2201/09018; H05K 2201/09027; Y10T 29/49117; Y10S 362/80; H01S 5/02476; A61B 1/0607; A61B 1/0684; A61B 2019/521; G11B 2005/0021; H05B 33/0803; A01K 63/06; B29K 2995/0013; F21S 48/215; F21S 4/003; F21S 8/02; F21S 48/328; F21S 4/008; F21S 8/026; F21L 4/00; G02B 19/0061; G02B 6/4269; G02B 6/4272; G02B 6/4296
USPC ......... 362/551, 555, 557, 572, 573, 574, 575, 362/577, 119, 120, 109, 118
See application file for complete search history.

(56) References Cited

U.S. PATENT DOCUMENTS 5,471,129 A 11/1995 Mann
(Continued)

*Primary Examiner* — Mary McManmon
*Assistant Examiner* — Danielle Allen
(74) *Attorney, Agent, or Firm* — Louis J. Franco; Law Office of Louis J. Franco

(57) ABSTRACT

A light-emitting wand is configured for selective cooperative coupling with a handset. The wand extends between longitudinally opposed wand-body proximal and distal ends, the distal end being configured to retain a light-emitting element. Extending in mutual parallel alignment between the proximal and distal ends are electrically-conductive first and second core members. Each core member has, at the distal end, a light-source contact configured for electrical contact with a respective pole of the light-emitting element and, at the proximal end, a power-source contact configured for electrical contact with a respective terminal of an electrical-power source. The core members are maintained in mutual electrical isolation and overmolded with an electrically-insulative material through which the power-source contacts are exposed in order to enable selective electrical connection with electrical-power source terminals. In addition to carrying electrical current, the core members serve as heat sinks to dissipate the thermal output of the light-emitting element.

10 Claims, 4 Drawing Sheets

(51) Int. Cl.
   *F21V 29/00*   (2015.01)
   *G02B 19/00*   (2006.01)
   *A61B 17/00*   (2006.01)
   *A61B 19/00*   (2006.01)

(56) References Cited

U.S. PATENT DOCUMENTS

| | | |
|---|---|---|
| 6,331,111 B1 | 12/2001 | Cao |
| 6,468,077 B1 | 10/2002 | Melikechi et al. |
| 6,702,576 B2 | 3/2004 | Fischer et al. |
| 6,755,648 B2 | 6/2004 | Cao |
| 6,926,524 B2 | 8/2005 | Cao |
| 6,971,875 B2 | 12/2005 | Cao |
| 6,988,891 B2 | 1/2006 | Cao |
| 6,994,546 B2 | 2/2006 | Fischer et al. |
| 7,056,116 B2 | 6/2006 | Scott et al. |
| 7,077,648 B2 | 7/2006 | Cao |
| 7,086,858 B2 | 8/2006 | Cao |
| 7,094,054 B2 | 8/2006 | Cao |
| 7,320,593 B2 | 1/2008 | Ostler et al. |
| 7,581,846 B2 | 9/2009 | Hayman et al. |
| 8,591,057 B2 * | 11/2013 | Kawabata et al. ....... 362/217.02 |
| 2002/0133970 A1 | 9/2002 | Gordon et al. |
| 2002/0177099 A1 * | 11/2002 | Cao ............................... 433/29 |
| 2002/0197582 A1 | 12/2002 | Cao |
| 2003/0113684 A1 | 6/2003 | Scott |
| 2005/0142514 A1 | 6/2005 | Scott |

* cited by examiner

LIGHT-EMITTING WAND WITH ELECTRICALLY-CONDUCTIVE HEAT SINKS

PROVISIONAL PRIORITY CLAIM

Priority based on Provisional Application Ser. No. 61/464,930 filed Mar. 11, 2011, and entitled "LIGHT-EMITTING WAND WITH ELECTRICALLY-CONDUCTIVE HEAT SINKS" is claimed. The entirety of the disclosure of the previous provisional application, including the drawings, is incorporated herein by reference as if set forth fully in the present application.

BACKGROUND

Light-emitting wands find various applications across numerous industries such as, by way of non-limiting example, the curing of photosensitive compounds used in dentistry. Traditionally, such wands incorporated a light-emitting element such as an incandescent light bulb. Increasingly, however, light-emitting diodes (LEDs) have replaced incandescent bulbs.

Regardless of the light-emitting element used in a light-emitting wand, the efficient removal of heat generated by the light-emitting element is a widely recognized concern that has been the subject of alternative solutions of varying success. Some solutions have involved the inclusion of fans in the vicinity of the light-emitting element, an arrangement that, while effective, adds undesirable bulk to the wand. In at least one case, a phase change material is encapsulated in a thermally conductive container situated adjacent the light-emitting element and absorbs heat in changing from a first to a second phase. Numerous alternative designs have involved the inclusion of thermally-conductive heat sink material along some portion of the wand length. However, the inclusion of heat sinks along with separate electrical components (e.g., wires) required to deliver electrical current to the light-emitting element has resulted in wands of unwanted mass and larger-than-desired spatial dimensions.

Accordingly, there exists a need for a light-emitting wand that facilitates the effective removal of heat from, and the delivery of electric current to, a light-emitting element situated at a distal end thereof in a more spatially-efficient and mass-efficient manner.

SUMMARY

In one illustrative embodiment, a light-emitting wand is configured for selective cooperative coupling with a handset that serves as a handle and provides electrical power to a light-emitting element retained by the light-emitting wand. The light-emitting wand has an elongated wand body extending along a wand axis between longitudinally opposed proximal and distal ends of the body. The distal end is configured to support a light-emitting element such as, by way of non-limiting example, a light-emitting diode (LED) or a light bulb. In alternative versions, the light-emitting element is one of (i) selectively removable in order to facilitate replacement and (ii) permanently affixed within the distal wand end.

Included within the body of an illustratively configured wand are electrically-conductive first and second core members that extend longitudinally between the proximal and distal ends of the wand. The electrically-conductive first core member has, at the distal end, a first light-source contact configured for electrical connection to a first pole of the light-emitting element and, at the proximal end, a first power-source contact configured for electrical connection to a first terminal of an electrical-power source. Analogously, the electrically-conductive second core member includes at, respectively, the distal and proximal wand ends, a second light-source contact configured for electrical connection to a second pole of the light-emitting element and a second power-source contact configured for electrical connection to a second terminal of the electrical-power source.

The wand is configured to maintain the first and second core members in mutual electrical isolation. In one embodiment, there is disposed between the first and second core members an electrically-insulative partition. In a particular version including an electrically-insulative partition made from a polymeric material such as plastic, the partition is integrally formed with an electrically-insulative overmold that defines a wand-body side wall and encapsulates at least a portion of the length of each of the first and second core members.

In each of various embodiments, the wand body includes a coupling base that is at least partially coextensive with the wand-body proximal end. In one illustrative version, the coupling base is configured for selective receipt and retention by a coupling socket in a handset. The first and second power-source contacts and overmold are configured such that the power-source contacts are at least partially exposed through the overmold in order to facilitate selective electrical connection to respective terminals of the electrical power source. In accordance with one configuration, at least a portion of the length of the overmold defines a cylindrical side wall portion coinciding with, and partially defining, the coupling base. Each of the power-source contacts presents to the exterior of the overmold a convex arcuate contact surface configured to conform to the cylindrical side wall portion.

In addition to carrying electrical current between the power source and the light-emitting element, the core members serve as heat sinks configured for drawing heat away from the light-emitting element. In one illustrative version, each of the core members is comprised of copper. However, it will be appreciated that numerous alternative materials could substitute for copper in the composition of the core members.

Representative, non-limiting embodiments are more completely described and depicted in the following detailed description and the accompanying drawings.

DETAILED DESCRIPTION

The following description of variously embodied light-emitting wands and handsets configured for cooperative coupling therewith is illustrative in nature and is therefore not intended to limit the invention or its application of uses. The various implementations, aspects, versions and embodiments described in the summary and detailed description are in the nature of non-limiting examples falling within the scope of the appended claims and do not serve to constrain the maximum scope of the claims.

Figure 1:
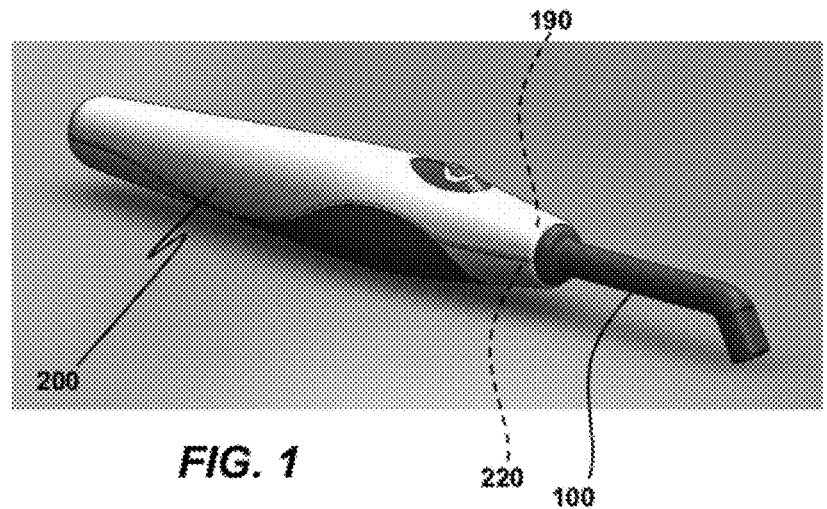
FIG. 1 shows a light-emitting wand cooperatively coupled with a handset.
Figure 1A:
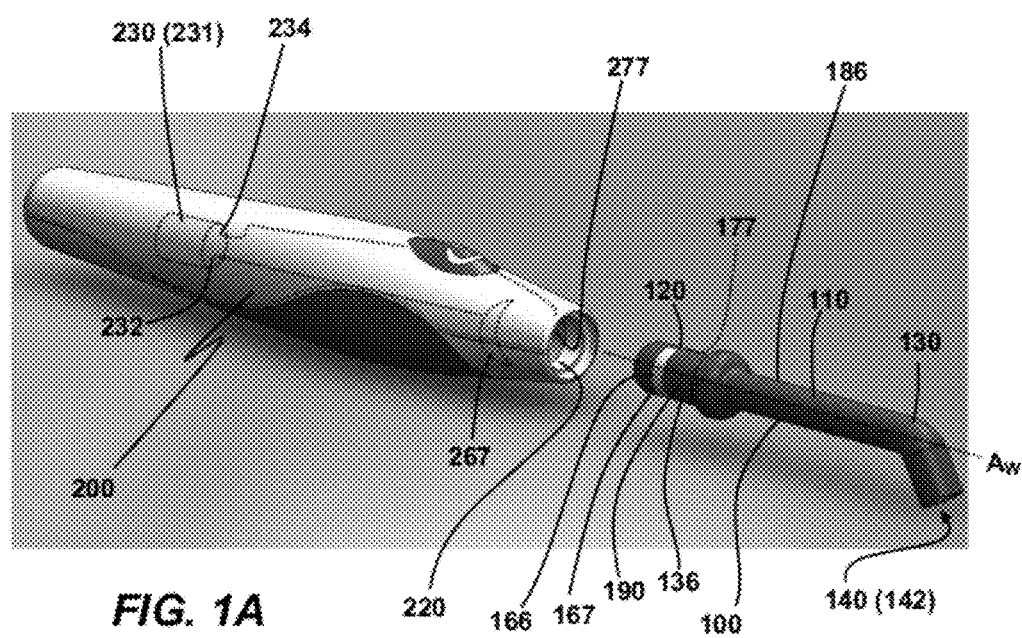
FIG. 1A depicts the light-emitting wand and handset of FIG. 1 decoupled from one another.

Referring initially to FIGS. 1 and 1A, an illustrative light-emitting wand 100 is selectively coupleable and separable from a handset 200. The handset 200 serves as a handle and delivers electrical power to the light-emitting wand 100. Although the ultimate source of electrical power to the wand 100 is of no particular consequence, alternatively embodied handsets 200 either (i) house a self-contained power source, such as a battery or (ii) have power delivered to them from an external source, such as a power cord configured for plugging into an electrical socket.

Figure 2:
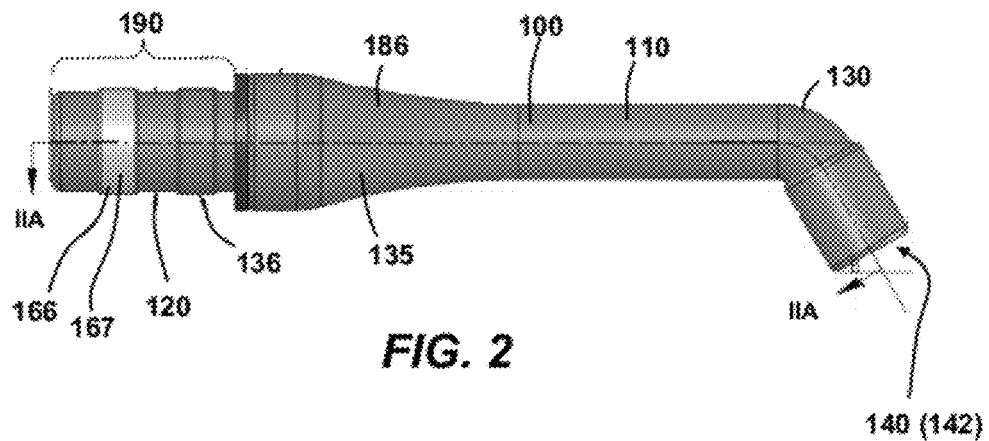
FIG. 2 is a right-side view of an illustrative light-emitting wand in isolation.

As shown more clearly in FIG. 1A, in which the wand 100 is separated from the handset 200, and FIG. 2, which shows the right side of a wand 100 in isolation, the wand 100 has an elongated wand body 110 that extends along a wand axis $A_w$ between longitudinally opposed wand-body proximal and distal ends 120 and 130. The distal end 130 is configured for retention of a light-emitting element 140 such as, by way of non-limiting example, a single light-emitting diode 142 (LED) or an assembly of two or more light-emitting diodes 142.

Figure 2A:
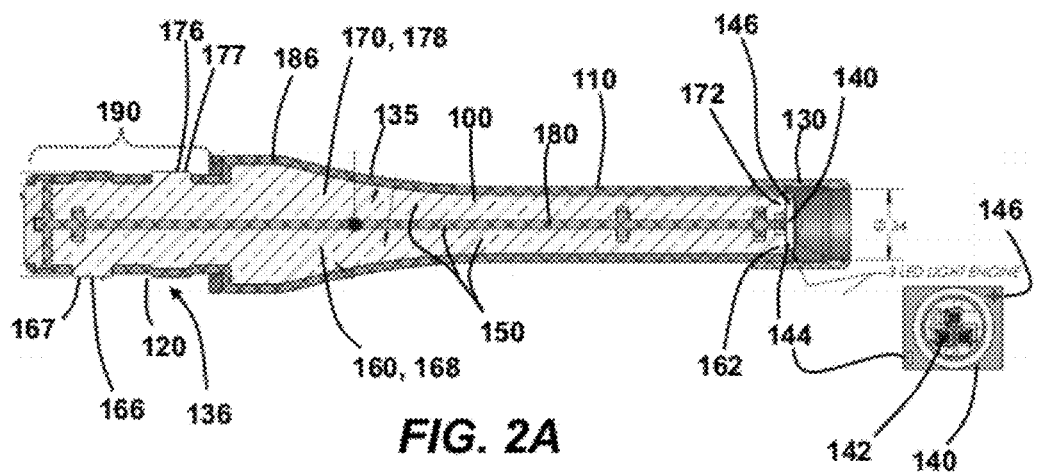
FIG. 2A is a sectional view of the light-emitting wand of FIG. 2 as viewed into the curvo-planar Section IIA indicated in FIG. 2.
Figure 3:
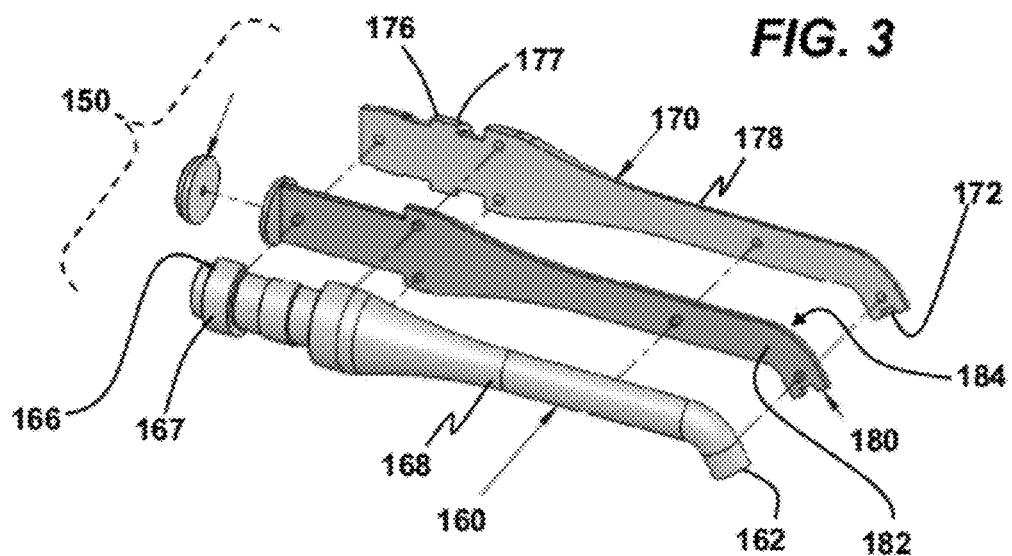
FIG. 3 is an exploded view of the core assembly details of the light-emitting wand shown in FIGS. 2 and 2A.

Referring to the sectional and exploded views of, respectively, FIGS. 2A and 3, the wand body 110 includes a core assembly 150 comprising electrically-conductive first and second core members 160 and 170 that longitudinally extend in mutual parallel alignment between the wand-body proximal and distal ends 120 and 130. The first core member 160 has, at the distal end 130, a first light-source contact 162 configured for electrical connection to a first pole 144 of the light-emitting element 140 and, at the proximal end 120, a first power-source contact 166 configured for electrical connection to a first terminal of an electrical-power source. The second core member 170 includes at, respectively, the distal and proximal wand-body ends 130 and 120, a second light-source contact 172 configured for electrical connection to a second pole 146 of the light-emitting element 140 and a second power-source contact configured for electrical connection to a second terminal of the electrical-power source.

Figure 3A:
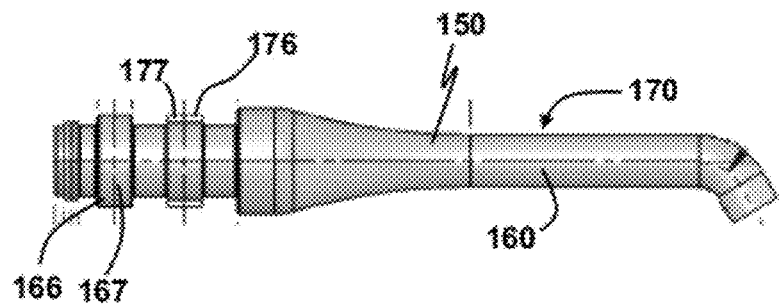
FIG. 3A is a left-side view of the assembled core assembly of FIG. 3.
Figure 3B:
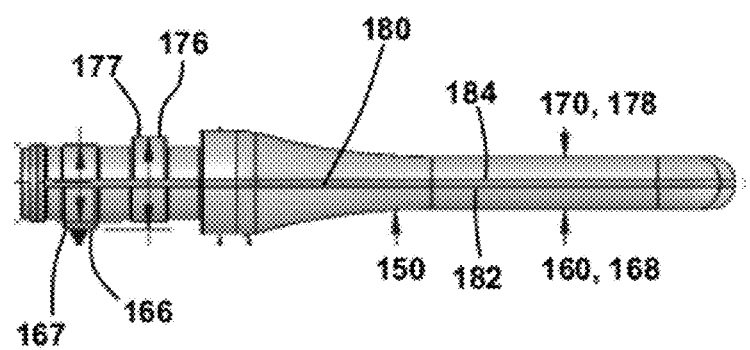
FIG. 3B is a top view of the assembled core assembly of FIGS. 3 and 3A.
Figure 4:
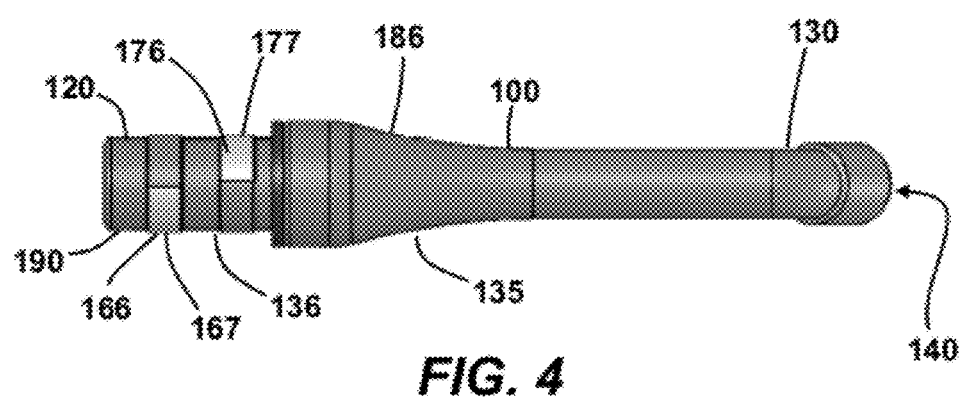
FIG. 4 is a top view of a light-emitting wand comprising an overmolded core assembly.

The core assembly 150 of the wand 100 is configured to maintain the first and second core members 160 and 170 in mutual electrical isolation. With continued reference to FIGS. 2A and 3, an electrically-insulative partition 180 is situated between the first and second core members 160 and 170. In one illustrative version, the partition 180 is a standalone component "preformed" from a polymeric material such as plastic. The partition 180 is situated between the first and second core members 160 and 170, and the core members 160 and 170 are urged toward one another to form a core assembly 150 as shown in the right-side and top views of, respectively, FIGS. 3A and 3B, in which the first core member 160 is in contacting engagement with a first side 182 of the partition 180 and the second core member 170 is in contacting engagement with a second side 184 of the partition 180. The core assembly 150 is then sealed in an overmold 186 of electrically-insulative material such as plastic, by way of non-limiting example, to form the wand body 100, as shown in previously-referenced FIGS. 2 and 2A, and the top view of FIG. 4. In an alternative version, the core members 160 and 170 are placed in a mold (not shown) such that a gap is maintained between them. An electrically-insulative material is then introduced (e.g., injected) into the mold to integrally form the partition 180 and the overmold 186 in a single molding step. In either case, as shown in FIGS. 2, 2A and 4, the overmold defines a wand-body side wall 135 that encapsulates at least a portion of the length of each of the first and second core members 160 and 170.

In the illustrative depictions of FIGS. 1A, 2 and 2A, for example, a portion of the wand-body side wall 135 defined by the overmold 186 defines a coupling base 190 that is at least partially coextensive with the wand-body proximal end 120. As shown in FIGS. 1 and 1A, the coupling base 190 is configured for selective receipt and retention by a coupling socket 220 defined in the handset 200. As shown most clearly in FIGS. 1A, 2, 2A and 4, the overmold 186 and the first and second power-source contacts 166 and 176 are configured such that the power-source contacts 166 and 176 are at least partially exposed through the overmold 186 in order to facilitate selective electrical connection to (e.g., contact with) respective terminals of the electrical power source 230 in the handset 200. More specifically, in the embodiments variously depicted in the drawings, at least a portion of the length of the overmold 186 defines a cylindrical side wall portion 136 coinciding with, and partially defining, the coupling base 190. The first and second power-source contacts 166 and 176 present to the exterior of the overmold 186, respectively, convex arcuate first and second contact surfaces 167 and 177 configured to conform to the cylindrical side wall portion 136. The convex arcuate first and second contact surfaces 167 and 177 are configured for contacting engagement with corresponding concave arcuate first and second power-delivery contacts 267 and 277 defined within the coupling socket 220 of the handset 200 and constituting, or leading to, respective first and second terminals 232 and 234 of a power source 230, as indicated primarily in phantom in FIG. 1A. In FIG. 1A, the power source 230 is illustratively depicted as a battery 231. However, as previously explained, the power source 230 could deliver electrical current through, for example, a power cord and electrical outlet such as a wall or floor socket (not shown).

In addition to carrying electrical current between the power source 230 and the light-emitting element 140, the first and second core members 160 and 170 serve as, respectively, first and second heat sinks 168 and 178 configured for dissipating the thermal output of the light-emitting element 140. Factoring into the capacity of each of the core members 160 and 170 to draw heat away from the light-emitting element 140 are the shape, mass, specific heat, and thermal conductivity of the core members 160 and 170. In addition, the extent to which each of the core members 160 and 170 is overmolded factors into its capacity to dissipate heat.

In one illustrative version, each of the core members 160 and 170 is comprised of copper. However, it will be appreciated that numerous alternative materials could substitute for copper in the composition of the core members 160 and 170. It will be furthermore appreciated that electrical conductivity—and, perhaps electrical conductivity as a function of temperature—is also to be considered in selecting material(s) from which to fabricate the core members 160 and 170. When the light-emitting element 140 comprises one or more light-emitting diodes (LEDs) 142, thermal output can be considerable. In the version of FIG. 2A, the illustrative light-emitting element 142 is an "LED engine" containing three light-emitting diodes 142. An enlarged and rotated detail of the LED engine is depicted adjacent the wand-body distal end 130 in FIG. 2A.

The foregoing is considered to be illustrative of the principles of the invention. Furthermore, since modifications and changes to various aspects and implementations will occur to those skilled in the art without departing from the scope and spirit of the invention, it is to be understood that the foregoing does not limit the invention as expressed in the appended claims to the exact constructions, implementations and versions shown and described.

What is claimed is:

1. A light-emitting wand comprising:
   an elongated wand body extending along a wand axis between longitudinally opposed wand-body proximal and distal ends, the distal end being configured to support a light-emitting element;
   an electrically-conductive first core member extending between the proximal and distal ends and having, at the distal end, a first light-source contact configured for electrical connection to a first pole of the light-emitting element and, at the proximal end, a first power-source contact configured for electrical connection to a first terminal of an electrical-power source;
   an electrically-conductive second core member extending between the proximal and distal ends and having, at the distal end, a second light-source contact configured for electrical connection to a second pole of the light-emitting element and, at the proximal end, a second power-source contact configured for electrical connection to a second terminal of the electrical-power source; wherein
   (i) the wand body comprises an electrically-insulative partition situated between, and configured to mutually electrically isolate, the first and second core members; and
   (ii) each of the first and second core members is a heat sink configured for drawing heat away from the light-emitting element.

2. The light-emitting wand of claim 1 wherein the wand body further comprises an electrically-insulative overmold that defines a wand-body side wall and encapsulates at least a portion of the length of each of the first and second core members.

3. The light-emitting wand of claim 2 wherein the overmold is integrally formed with the partition.

4. The light-emitting wand of claim 3 wherein the power-source contact of each of the first and second core members is exposed through the wand-body side wall in order to facilitate selective electrical connection to, respectively, the first and second terminals of the electrical power source.

5. The light-emitting wand of claim 4 wherein (i) at least the portion of the length of the overmold through which the first and second power-source contacts are exposed defines a cylindrical side wall portion and (ii) each of the power-source contacts presents to the exterior of the overmold a convex arcuate contact surface configured to conform to the cylindrical side wall portion.

6. The light-emitting wand of claim 2 wherein the power-source contact of each of the first and second core members is exposed through the body side wall in order to facilitate selective electrical connection to, respectively, the first and second terminals of the electrical power source.

7. The light-emitting wand of claim 6 wherein (i) at least the portion of the length of the overmold through which the first and second power-source contacts are exposed defines a cylindrical side wall portion and (ii) each of the power-source contacts presents to the exterior of the overmold a convex arcuate contact surface configured to conform to the cylindrical side wall portion.

8. The light-emitting wand of claim 7 wherein the power-source contacts are longitudinally offset from one another such that the contact surface of one of power-source contacts is more proximate the distal end of the wand body than is the contact surface of the other power-source contact.

9. The light-emitting wand of claim 6 wherein the power-source contacts are longitudinally offset from one another such that the contact surface of one of power-source contacts is more proximate the distal end of the wand body than is the contact surface of the other power-source contact.

10. The light-emitting wand of claim 2 wherein the light-emitting element comprises a light-emitting diode.

* * * * *